United States Patent [19]

Strazielle et al.

[11] Patent Number: 5,507,638
[45] Date of Patent: Apr. 16, 1996

[54] REWARD-BASED APPARATUS FOR THE REHABILITATION OF LABIOLINGUAL FUNCTIONS

[76] Inventors: Catherine G. Strazielle, 32, rue du Temeraire, Nancy F-54000; Roland Alard, 4, Bd Jean-Jaures, Tomblaine F-54510, both of France

[21] Appl. No.: 178,235
[22] PCT Filed: May 7, 1993
[86] PCT No.: PCT/FR93/00440
  § 371 Date: Jan. 7, 1994
  § 102(e) Date: Jan. 7, 1994
[87] PCT Pub. No.: WO93/21852
  PCT Pub. Date: Nov. 11, 1993

[30] Foreign Application Priority Data

May 7, 1992 [FR] France .................................. 92 05841

[51] Int. Cl.⁶ .................................................. A61C 3/00
[52] U.S. Cl. .................................. 433/6; 433/7; 433/21
[58] Field of Search .................... 433/6, 7, 18, 21, 433/24; 128/859, 860, 861, 862

[56] References Cited

U.S. PATENT DOCUMENTS

| | | | |
|---|---|---|---|
| 3,434,210 | 3/1969 | Sage | 433/7 |
| 3,454,001 | 7/1969 | Stockfisch | 433/6 X |
| 3,827,146 | 8/1974 | Wallshein | 433/7 |
| 4,026,023 | 5/1977 | Fisher | 433/7 |
| 4,028,808 | 6/1977 | Schwartz | 433/7 |
| 4,054,996 | 10/1977 | Wallshein | 433/7 |
| 4,202,100 | 5/1980 | Forster | 433/7 |
| 4,516,936 | 5/1985 | Hulsink | 433/6 |
| 5,002,485 | 3/1991 | Aagesen | 433/18 X |
| 5,064,370 | 11/1991 | Jones | 433/18 X |
| 5,096,416 | 3/1992 | Hulsink | 433/6 |

FOREIGN PATENT DOCUMENTS

| | | | |
|---|---|---|---|
| 981973 | 6/1951 | France | 433/7 |
| 1736463 | 5/1992 | U.S.S.R. | 433/7 |

*Primary Examiner*—Nicholas D. Lucchesi
*Attorney, Agent, or Firm*—Weiser & Associates

[57] ABSTRACT

An intraoral apparatus for the treatment of labiolingual dysfunctions which includes a removable support plate equipped with dental anchoring hooks and an anterior vestibular arc. The apparatus includes an active device, and attachment members and stimulating elements which are attached to the support plate for stimulating exact positions within the oral cavity that are associated with various orofacial functions.

10 Claims, 1 Drawing Sheet

5,507,638

REWARD-BASED APPARATUS FOR THE REHABILITATION OF LABIOLINGUAL FUNCTIONS

BACKGROUND OF THE INVENTION

The present invention relates to an intraoral apparatus for functional rehabilitation which is used in subjects suffering from labiolingual dysfunctions.

In functional disorders (of phonation, deglutition, respiration, food ingestion, ect.) involving the orofacial sphere it is necessary for the functions to be restored. In the correction of maxillofacial dysmorphoses associated with labiolingual dysfunctions, it is imperative to carry out a functional reeducation of the oral and perioral muscle masses.

The apparatus of the present invention is indeed:

to replace the type of punitive devices which have been used hitherto and, to replace or reinforce by a permanent and unconscious action, the myofunctional therapy techniques.

The principle of reeducation on which this apparatus is based relies on the importance of the role of reward and search for satisfaction in functional memorizing and learning.

SUMMARY OF THE INVENTION

It is an object of the present invention to provide an apparatus equipped with a fixing device which makes it possible to place various stimulating elements at the exact positions in the oral cavity which normally have to be stimulated in the various orofacial functions, both at the level of the upper jaw and the lower jaw. This attachment system permits a safe, quick and easy fixing of the stimulating elements.

The stimulating elements permit:

a permanent stimulation of the structural tissue zone involved in the function, with the apparatus being worn continuously, the maintenance of a "meaningful signal" necessary for so that memorizing of a learning process. The variability in the sensations experienced makes it possible to prevent habituation of the movement, the development of the oral muscles by exercise, the reinforcement of the memorizing and of the cerebral engramming of the reeducated functions, by the activation of the reward circuits associated with satisfaction, the placement of the active device on devices correcting associated maxillofacial dysmorphoses.

The apparatus is produced in the dental prosthesis laboratories using molds taken from impressions of the upper and lower jaws of the subject in question, and includes a removable support plate which can be formed of a material selected from the group consisting of resins, precious metals or semi-precious metals and which is equipped with dental anchoring hooks and an anterior vestibular arc (neutral or active). The active fixing device includes an attachment system which serves as a means for fixing the various stimulating elements having a satisfying physiological components (tubes, balls, sweets, cups, ect.).

DETAILED DESCRIPTION OF PREFERRED EMBODIMENTS

The attachment system of the present invention is generally comprised of two arms (of which one is freely movable) which are equipped with two helical spring members. The latter contribute to giving a certain elasticity to the wire used. A posterior spring member permits the locking of a free arm of the attachment in a closure position. An anterior spring member defines an opening of the attachment, necessary for placement of the stimulating elements.

The attachment system is made in the intrados of the apparatus for two reasons:

complete safety, it being possible for the attachment to be opened only after the apparatus has been removed from the mouth, the device does not interfere with the awareness of the oral sensations present in each function.

Figure 1:
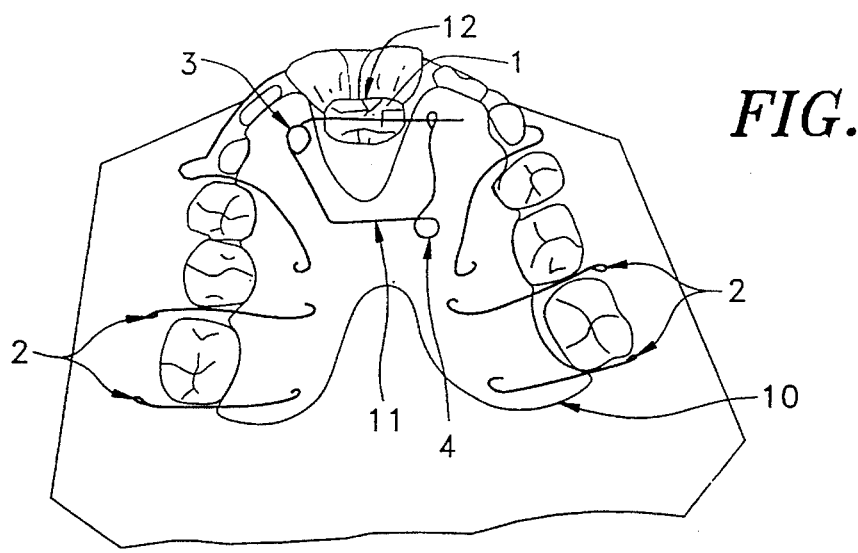
FIG. 1 is a top plan view of the apparatus of the present invention in position on a standard model.

FIG. 1 shows the apparatus in position on a standard model. This is a specific embodiment for the reeducation of the deglutition function.

The active device (1) is placed set back behind the incisors, perpendicular to the median raphe, its anterior part being raised above the papillae by two spring members. As a non-limiting example.

The plate 10 is made of a powdered and monomeric resin and the hooks 2 are of the "spur" type, thereby permitting "clamping" adjustment which thus ensures a good posterior retention of the apparatus. The apparatus is represented here, by way of example, with a granular oval ball as the stimulating element 12.

The type of hooks 2 used, the materials selected and the limits of the support plate 10 are not active elements of the reeducative technique. Consequently, the manufacture of these elements does not necessitate any particular choice of materials, shapes and dimensions. These elements are determined as a function of the molds, which are representative of the subject being tested.

Figure 2:
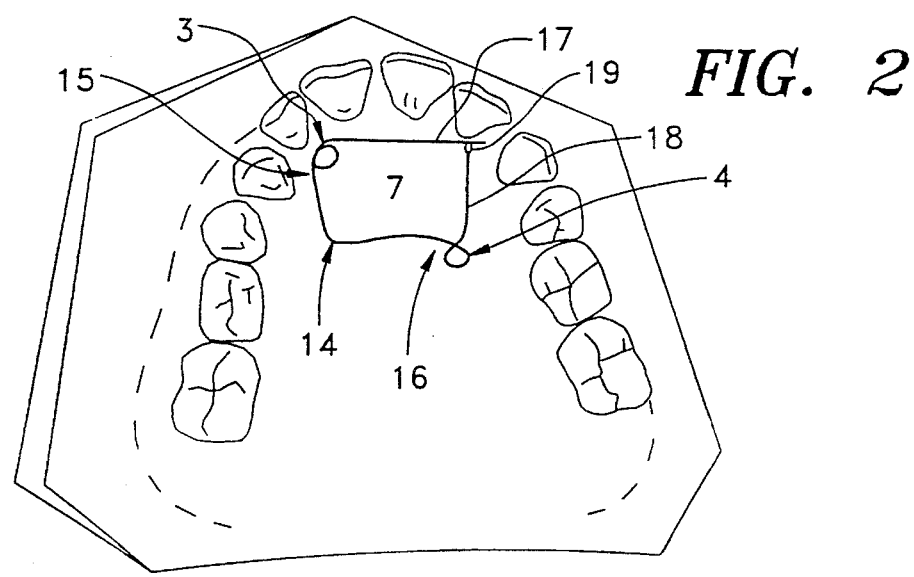
FIG. 2 is a top plan view which schematically illustrates the attachment system of FIG. 1, with structure removed to reveal construction detail.

FIG. 2 shows the attachment system 14, equipped with an anterior spring member 3 and a posterior spring member 4 (as viewed from above), with the structure of the plate 10 and the hooks 2 removed to better reveal the structure which remains. The attachment system 14 includes a first wire portion 15 connected to a second wire portion 16. The first wire portion 15 has an anterior spring member 3 with a first arm 17 which is freely movable. The second wire portion 16 has a posterior spring member 4 with a second arm 18 located perpendicular to the first arm 17, and is provided with a looping structure 19 for receiving the free end of the first arm 17, thereby latching the first arm 17 in a closed position. When the first arm 17 is free, i.e., in an open position, the active device 1, and the stimulation elements 12, can be placed or replaced, as desired. The attachment system 14 sits within the anterior vestibular arc, or intrados 11, of the support plate 10.

Figure 3:
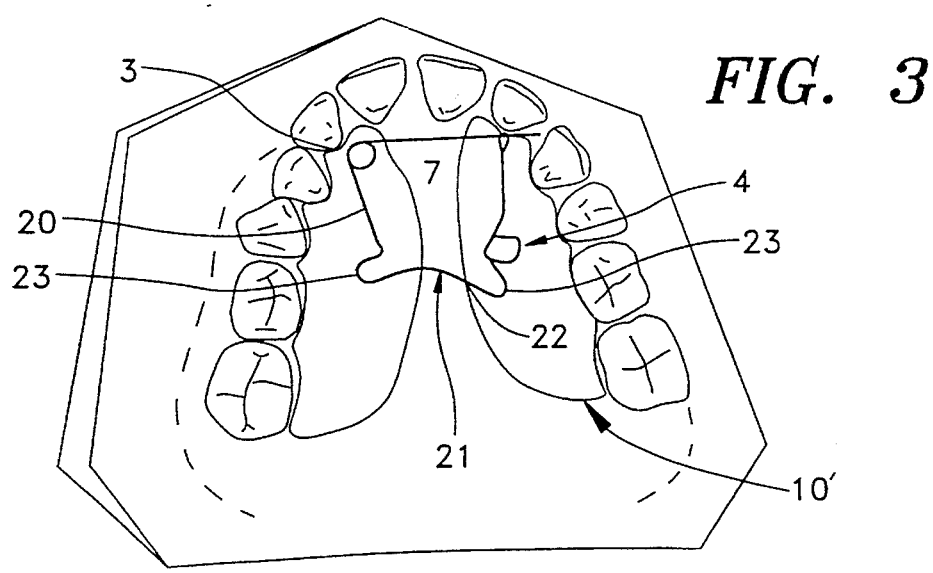
FIG. 3 is a top plan view similar to FIG. 2, which schematically illustrates a variation of the attachment system of the present invention.

FIG. 3 shows a variant 20 of the attachment system having a transverse expansion jack 21 (in association with the alternative embodiment plate 10' shown in FIG. 3). In this embodiment, the posterior spring member 22 is modified, and includes two supporting rounded sections 23 which are included in the material of the support plate 10. In this embodiment it is necessary, in a second stage, to saw the posterior spring member 22 in order to open the expansion jack 21.

By way of non-limiting example, the foregoing devices are manufactured with a steel wire of a diameter of 7/10 mm.

The above descried devices are used in the rehabilitation of orofacial functions, and are intended for therapeutic purposes. The support plate 10 is produced individually on molds taken from individual impressions from the subjects under treatment. Only the attachment system of the present invention can be manufactured in series on the basis of pre-established standardized models.

We claim:

1. An intraoral apparatus for rehabilitating labiolingual functions, comprising a support plate, and means for removably fixing a stimulation element for labiolingual rehabilitation to the support plate, wherein the fixing means includes an attachment system including two helical spring members, wherein one of the spring members is an anterior spring member for extended movement of an active arm associated with the anterior spring member, for receiving the fixing means and for raising the fixing means relative to osseous tissues and corresponding mucosa, and wherein another of the spring members is a posterior spring member forming a safety closure for the attachment system.

2. The intraoral apparatus of claim 1 wherein the apparatus includes an intrados for receiving the fixing means.

3. The intraoral apparatus of claim 1 wherein the attachment system is mounted on a support plate adapted for association with a subject for treatment.

4. The intraoral apparatus of claim 3 wherein the support plate is formed of a material selected from the group consisting of resins, precious metals or semi-precious metals.

5. The intraoral apparatus of claim 3 which further includes dental anchoring hooks associated with the support plate, for retaining the apparatus in position.

6. An intraoral apparatus for rehabilitating labiolingual functions, comprising a support plate having an anterior intrados, means for maintaining the support plate in position, and an attachment system mounted on the support plate and including a safety closure which removably holds at least one stimulation element in the anterior intrados of the support plate for stimulating the labiolingual functions.

7. The intraoral apparatus of claim 6 wherein the attachment system includes an anterior wire portion connected to a posterior wire portion, wherein the anterior wire portion has a spring member with a first arm which is freely movable, and the posterior wire portion has a spring member with a second arm having means for maintaining the first arm in a closed position, such that in an open position, the first arm allows placement and replacement of the active device with the stimulation element.

8. The intraoral apparatus of claim 6 wherein the means for maintaining the support plate in position are hooks.

9. The intraoral apparatus of claim 6 wherein the support plate is formed of a material selected from the group consisting of resins, precious metals or semi-precious metals.

10. The intraoral apparatus of claim 6 wherein the attachment system further includes a transverse expansion jack having two supporting rounded sections.

* * * * *